United States Patent [19]
Wagner et al.

[11] Patent Number: 5,912,390
[45] Date of Patent: Jun. 15, 1999

[54] METHOD FOR THE WORK-UP OF A SURFACTANT-CONTAINING REACTION MIXTURE

[75] Inventors: Ortwin Wagner, Mayen; Reinhard Schomäcker, Leverkusen, both of Germany

[73] Assignee: Bayer Aktiengesellschaft, Leverkusen, Germany

[21] Appl. No.: 08/568,055

[22] Filed: Dec. 6, 1995

[30] Foreign Application Priority Data

Dec. 15, 1994 [DE] Germany .................. 44 44 739

[51] Int. Cl.⁶ .................................................. C07C 41/40
[52] U.S. Cl. .................. 568/630; 516/194; 516/925; 568/579
[58] Field of Search ................... 252/303, 312, 252/314; 568/630, 579; 516/194, 195, 196, 923, 925

[56] References Cited

U.S. PATENT DOCUMENTS

| | | | |
|---|---|---|---|
| 549,728 | 11/1895 | Kraft et al. | 568/630 |
| 797,024 | 8/1905 | Sparre | 568/630 |
| 1,801,901 | 4/1931 | Britton et al. | 568/630 |
| 2,445,500 | 7/1948 | Tyrer | 568/630 |
| 3,641,181 | 2/1972 | Robbins et al. | 252/312 |
| 3,855,269 | 12/1974 | Childs | 558/463 |
| 4,595,763 | 6/1986 | Renga et al. | 568/630 |
| 4,835,321 | 5/1989 | Leach et al. | 568/618 |

FOREIGN PATENT DOCUMENTS 0038986  11/1981  European Pat. Off. .

OTHER PUBLICATIONS

Drew Myers, "Surfactant Science and Technology", (VCH Publishers, NY, NY copyright 1992), pp. 66–67.
Milton J. Rosen, "Surfactants and Interfacial Phenomena", (John Wiley & Sons, Ny, NY, copyright 1978) p. 17.
S. Benita, Microemulsion Methods and Industrial Applications, (Marcel Dekker, Inc., NYU, NY) pp. 593–594, Jun. 1995.
L. Prince, Microemulsions Theory and Practice, (Academic Press, Inc., NY, NY) pp. 1–2, 1977.
F.M. Menger et al, J.Am.Chem.Soc., vol. 113, pp. 9621–9624 (1991).
Derwent Abstracts, Abstract of JP 59–112,839 (1984) Week 8432.
Nachrichten aus Chemie Technik und Laboratorium, vol. 40, No. 12, pp. 1344 and 1346–1348, (1992).
Chemical Abstracts, vol. 95, p. 34, abstract of DE 3,016,112, (1980).

*Primary Examiner*—Richard D. Lovering
*Assistant Examiner*—Daniel S. Metzmaier
*Attorney, Agent, or Firm*—Sprung Kramer Schaefer & Briscoe

[57] ABSTRACT

A method for the work-up of a nonionic surfactant-containing microemulsion reaction mixture formed in the o-alkylation of phenols by an alkyl halide in the presence of sodium hydroxide. Said mixture has one reaction product present as an aqueous phase and a further reaction product present as a water immiscible phase and which the reaction mixture is obtained in microemulsion form. Said reaction mixture is worked up by:

a) subjecting this microemulsion to a temperature decreased by 20 to 50K thereby forming an aqueous phase having a high surfactant content and a substantially surfactant-free organic phase, b) separating off the substantially surfactant-free organic phase formed and replacing said surfactant-free organic phase with an organic solution of the alkyl halide. After the replacement of the substantially surfactant-free phase, c) the reaction mixture thus treated is subjected to a temperature increase by 10 to 80K thereby forming a substantially surfactant-free aqueous phase and a high surfactant content organic phase, d) the substantially surfactant-free aqueous phase is separated off and replaced by additional aqueous solution of phenols. The mixture then present can be fed again to the reaction.

10 Claims, No Drawings

METHOD FOR THE WORK-UP OF A SURFACTANT-CONTAINING REACTION MIXTURE

BACKGROUND OF THE INVENTION

The present invention relates to the work-up of a surfactant-containing reaction mixture arising as a microemulsion.

In many chemical reactions, the starting materials and, generally, also the products have solubilities so different that they can be dissolved together neither in one non-polar organic solvent nor in water. A typical example of this is the dehydrohalogenation of 3,4-dichloro-1-butene (water-insoluble) by sodium hydroxide which is added in the form of aqueous sodium hydroxide solution. Further examples are the formation of nitrites from alkyl halides and inorganic cyanides or various alkylation reactions in the presence of strong bases (Nachr. Chem. Techn. Lab. 40, (1992), 1344). The difficulties indicated can be counteracted, for example, as follows:

1. A polar organic solvent (for example methanol, dimethylformamide, acetonitrile) is used which dissolves both starting materials to a limited extent. The reaction then proceeds in a homogeneous phase.
2. The starting materials are dissolved in their preferred solvents and a large internal interface is generated by a dispersion means (for example by agitators or nozzles).
3. A phase-transfer catalyst is added to the starting materials dissolved in their solvents, which catalyst increases the solubility of one of the two reaction partners in the solvent of the other one.

However, the methods indicated generally have a disadvantage. Thus, polar organic solvents and phase-transfer catalysts are frequently environmentally polluting, for which reason it must be expected that their use will become increasingly more expensive owing to environmental restrictions and the necessity of a substantial work-up and therefore alternatives must generally be sought and found. The generation of a large phase interface by dispersion is generally only useful for rapid reactions, since in the case of slow reactions, because of the necessity of maintaining dispersions for a long period, much energy is required.

A novel method which does not have the disadvantages of the abovementioned methods is the generation of a microemulsion from the starting materials dissolved in their preferred solvents, by the addition of a surfactant (J. Am. Chem. Soc. 113 (1991), 9621). Such thermodynamically stable microemulsions contain highly fine droplets whose size is greatly below that of droplets generated by dispersion processes. Since the microemulsion forms spontaneously under certain conditions, that is is inherently stable, even slow reactions can be carried out particularly economically herein.

Whereas phase-transfer catalysts and dispersion processes are already used industrially, the use of microemulsion processes has, to date, not passed beyond the laboratory scale. This is due to the fact that microemulsions are only stable in a limited temperature range and concentration range of the starting materials. In order therefore to achieve stabilities sufficient for industrial use over a larger temperature range and to achieve an increase in starting material concentrations, increased surfactant concentrations are generally necessary. However, such increased surfactant concentrations in turn increase the necessity for work-up of such microemulsions, in order to recover substantially the surfactant used; this recovery at the same time prevents environmental pollution or corresponding countermeasures and, on the other hand, contamination of the product.

SUMMARY OF THE INVENTION

It has now been found that reaction mixtures in the form of microemulsions can be separated into multiphase systems by temperature changes described in more detail below, of which multiphase systems one phase in each case has a high surfactant content, while a further phase formed is substantially surfactant-free. The surfactant-free phase can easily be separated off and replaced in the overall system by a phase of the same type (either aqueous or water-immiscible organic phase).

The invention relates to a method for the work-up of a reaction mixture present as a microemulsion which has been formed by reaction of a first reaction partner which is present as an aqueous phase with a second reaction partner which is present as a water-immiscible liquid phase, in the presence of an anionic or nonionic surfactant and which reaction mixture, apart from the surfactant, contains a first reaction product which is soluble in water and a second reaction product which is soluble in water-immiscible organic solvents, the microemulsion being able to be present in coexistence with aqueous and with organic phase, which is characterized in that the reaction mixture initially present as a microemulsion a) is subjected to a temperature change by 20 to 50K to lower or to higher temperatures and by this means a phase having a high surfactant content and a substantially surfactant-free phase are obtained, b) the phase which is substantially surfactant-free and contains reaction products is separated off and an aqueous phase separated off is replaced by the aqueous phase of the first reaction partner and an organic phase separated off is replaced by the organic phase of the second reaction partner, c) the reaction mixture to be treated is subjected to a second temperature change by 10 to 80° C. in the opposite direction to the first temperature change and by this means, again, in addition to a phase having a high surfactant content, a substantially surfactant-free phase is obtained, d) the phase formed in c) which is substantially surfactant-free and contains reaction product is separated off and replaced in the manner mentioned under b) and e) the reactive mixture then present is again fed to the reaction.

DETAILED DESCRIPTION OF THE INVENTION

U.S. Pat. No. 3,855,269 discloses working up an emulsion which contains adiponitrile, acrylonitrile, if appropriate other organic compounds, inorganic salts, water and tetraalkylammonium salts by separating the reaction mixture which is present as an emulsion and is spontaneously separating and subjecting only the organic phase to a two-fold cooling.

JP 59/112 839 (1984) discloses extracting with water a quaternary ammonium salt which had been used as catalyst in the preparation of α-substituted benzyl cyanide from benzyl cyanide with alkyl halides; however, the reaction mixture to be extracted was not present as an emulsion and also originally did not contain water.

The reaction mixture to be worked up according to the invention, after the chemical reaction carried out has been completed, is present in the form of a microemulsion (ME) in the temperature range from 0 to 100° C., preferably from 30 to 80° C. This ME is now subjected according to the invention according to a) first to a temperature change in which the ME is passed to lower or to higher temperatures by 20 to 50K, starting from the temperature at which the ME arises. A change to low temperatures is limited by the freezing of the aqueous portion of the ME. However, this lower temperature is below 0° C. owing to the content of product and unreacted starting material in the water portion. The change to higher temperatures is limited by the boiling point of one portion of the ME. However, the boiling point can be shifted to higher temperatures by applying higher pressures. To this extent, the method according to the invention is employed at a pressure of 1 to 20 bar.

In the temperature change according to the invention as specified in a), in addition to a phase having a high surfactant content, a substantially surfactant-free phase forms. This substantially surfactant-free phase can be either an aqueous phase or a water-immiscible organic phase. This substantially surfactant-free phase is now separated off mechanically according to the invention as in b), for example by allowing to settle in separation vessels or by separating off in centrifuges, and is replaced by a phase of the same type containing new starting material. Of the same type in this context means that a substantially surfactant-free aqueous phase is replaced by an aqueous phase containing the water-soluble starting material and that a substantially surfactant-free organic, water-immiscible phase is replaced by the organic, water-immiscible starting material or by a solution of the organic starting material in a water-immiscible solvent.

According to the invention, after separation and replacement of the substantially surfactant-free phase in the above-described manner, a second temperature change is performed which is in the opposite direction to the first temperature change and which comprises the magnitude of 10 to 80K, preferably 20 to 60K. In this case also, the previously mentioned limits of ice formation or of not exceeding the boiling point are maintained. According to d), the substantially surfactant-free phase formed in c) is then also separated off and replaced by a phase of the same type; the mixture subsequently present now contains, in addition to the surfactant, both starting materials again and is again fed to the reaction.

The work-up method according to the invention can therefore be carried out in the following variants:

(i) The reaction mixture arising as ME reacted to completion is heated by 20 to 50K. In this case, in addition to the phase having a high surfactant content, a substantially surfactant-free phase forms. The fact of the formation of a substantially surfactant-free phase is a function of the type of the reaction partners, of their amounts, of the type and amount of surfactant used, thus quite generally of the composition of the ME, and of the temperature at which the reaction mixture reacted to completion arises and of the temperature to which it is brought by the temperature change according to the invention. Likewise a function of the said parameters is also the question of whether the substantially surfactant-free phase is an aqueous phase or a water-immiscible organic phase. In an analogous manner as described above, the substantially surfactant-free phase formed is separated off and replaced by a phase of the same type. This reaction mixture treated by temperature increase, phase removal and phase replacement is then subjected to a temperature reduction by 10 to 80K; again, in addition to a phase having a high surfactant content, a substantially surfactant-free phase forms. The type of the surfactant-free phase which forms in this second phase separation is of a different type (aqueous or organic) to the surfactant-free phase which has formed in the first phase separation. If, therefore, in the temperature elevation initially carried out, a surfactant-free organic phase had formed which had been replaced, in the temperature reduction a surfactant-free aqueous phase forms which is replaced, and vice versa.

(ii) The reaction mixture arising as ME reacted to completion, in an opposite manner to the variant under (i), is initially cooled by 20 to 50K, with, depending on the composition of the ME and depending on the temperatures of the ME obtained and its cooling, in addition to the phase having a high surfactant content, only one substantially surfactant-free phase being formed which, in the meaning of the material described above, can be an aqueous or an organic water-immiscible phase. This substantially surfactant-free phase is separated off and replaced in the meaning of the material described above, whereupon the now newly formed mixture is heated by 10 to 80K. After this heating a substantially surfactant-free phase arises again which is of the opposite type to the substantially surfactant-free phase initially arising. This is also separated off and replaced in the meaning of the material described above.

By both of the said variants (i) and (ii), a mixture is finally obtained of the phase having a high surfactant content and the two replaced phases (aqueous or organic) which, however, now in turn contain starting material for the intended reaction and thus can be fed again to the reaction. An ME is formed again here from by suitable temperature adjustment.

By simple preliminary experiments, those skilled in the art can determine which of the variants (i) or (ii) is used for an existing reaction mixture. Owing to the twofold temperature change and the separate removal of the two substantially surfactant-free phases, it is ensured that the reaction products are virtually completely separated off and recovered in the two phases separated off (aqueous and organic).

The process according to the invention can equally be carried out if, in the reaction mixture to be treated, the ME is present in coexistence with the aqueous phase and with the organic phase. This case occurs, for example, if the lower range of the amount of surfactant mentioned below is employed, starting materials and products alternate between the coexisting surfactant-free phases and the ME as reaction phase. Because of this, the amount of surfactant can be decreased in an economically and ecologically expedient manner. Based on the total reaction mixture, the amount of the ME is 50 to 100% by weight, preferably 70 to 100% by weight, the amount of the aqueous phase is 35 to 0% by weight, preferably 25 to 0% by weight, and the amount of the organic phase is 35 to 0% by weight, preferably 25 to 0% by weight.

Surfactants which are suitable for formation of the ME, which are returned to the reaction together with fresh starting materials by work-up according to the invention, are nonionic and anionic surfactants. These surfactants contrast with phase-transfer catalysts, which are cationic quaternary ammonium or phosphonium salts. Such quaternary salts are quite generally toxic to fish, from which there results the necessity for careful disposal. Furthermore, they can decompose, for instance by eliminating olefins from the quaternary ammonium or phosphonium group.

Nonionic surfactants for reaction mixtures to be worked up according to the invention are ethoxylates, propoxylates and mixed ethoxylate/propoxylates of alcohols, phenols, alkylphenols, carboxylic acids or carboxylic amides and long-chain fatty amines in which the basic molecule to be alkoxylated has 6 to 30 carbon atoms and the degree of alkoxylation comprises 4 to 40 ethylene oxide groups or propylene oxide groups. Preferably, in this case these are alkoxylated alcohols or phenols which are particularly preferably substituted by a $C_4$–$C_{16}$-alkyl chain. The alkyl chain in this case can be straight-chain or branched.

Anionic surfactants for the reaction mixture to be worked up according to the invention are, for example: alkyl sulphates, alkylsulphonates and alkyl carboxylates having alkyl chains having 4 to 18 carbon atoms. As cations, these surfactants can contain alkali metal ions or alkaline earth metal ions and ammonium ions.

The method according to the invention is preferably applied to those reaction mixtures which are present as ME which were formed using nonionic surfactants. In this case, one or a plurality of the said nonionic surfactants may be employed. Generally, nonionic surfactants arise anyway as a mixture of basic molecules alkoxylated to different extents, so that the specified degree of alkoxylation represents a mean value within a band width known to those skilled in the art. In many cases, it has been observed that when nonionic surfactants are used, a cooling within the meaning of the above variant (ii) is initially advantageously employed. In this case, in variant (ii), a substantially surfactant-free organic, water-immiscible product phase forms which is separated off and replaced by the organic starting material phase, while at the same time an aqueous phase having a high surfactant content forms.

The amount of surfactant which is contained in the reaction mixture arising as ME reacted to completion is 2 to 50% by weight, preferably 5 to 30% by weight, particularly preferably 7 to 20% by weight, based on the total weight of the reaction mixture.

The work-up method according to the invention is applicable to reaction mixtures reacted to completion and present as ME in which a multiplicity of reactions can have proceeded in which reaction partners have met each other, of which one was present predominantly in aqueous phase and the other as a water-immiscible organic phase. The reaction partner (starting material) present as organic phase can form alone the organic portion of the ME if it is liquid in the temperature range in question here. In the event that the water-insoluble organic reaction partner is gaseous or solid, it is used in the form of a solution in an organic water-immiscible solvent. Solvents which are suitable therefor are, for example: aliphatic $C_4$–$C_{20}$- or aromatic $C_6$–$C_{10}$-hydrocarbons which may be unsubstituted or substituted by halogen, nitro or ester groups and are familiar to those skilled in the art as typical organic solvents.

Reactions which lead to ME to be worked up according to the invention are, for example, the following the etherification, the dehydrohalogenation of halogenated hydrocarbons by aqueous alkali metal hydroxide, for example the dehydrochlorination of 3,4-dichloro-1-butene with NaOH, the formation of nitrites from alkyl halides and inorganic cyanides, the alkylation of alcohols, phenols, carboxylic acids, amines or amides using alkyl halides in the presence of strong bases, the α-alkylation of activated compounds using halogenoalkyls, e.g. the formation of α-alkylated nitrites from nitrites and halogenoalkyls, hydrolyses of esters in the presence of strong bases, oxidations of organic substances by bleaching lye, oxidations of organic substances by oxygen in the presence of water-soluble catalysts, reductions by water-soluble catalysts, oxidations of organic substances by $H_2O_2$ in the presence of water-soluble catalysts, oxidations by aqueous cerium (IV) sulphate solutions, acidic or alkaline eliminations of protecting groups.

Preferred reactions are:

the dehydrohalogenation of halogenated hydrocarbons, the formation of nitrites from alkyl halides and inorganic cyanides, the alkylation of alcohols, phenols, carboxylic acids, amines or amides, the α-alkylation of activated compounds or the hydrolysis of esters.

Such a process may be formulated as follows with reference to the O-alkylation of phenols by an alkyl halide in the presence of sodium hydroxide:

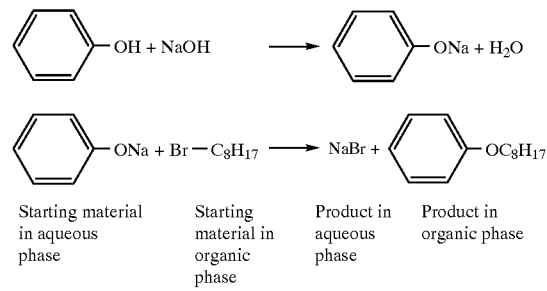

| Starting material in aqueous phase | Starting material in organic phase | Product in aqueous phase | Product in organic phase |

EXAMPLE

A reaction mixture in the form of a microemulsion (ME), in which n-octyl bromide and sodium phenolate, dissolved in water, had been reacted at 85° C., comprised 20% by weight of phenyl octyl ether, 60% by weight of 1 N NaBr solution and 20% by weight of the surfactant Triton X® (octylphenol+10 ethylene oxide units). This ME was cooled to 50° C. Two phases formed in this. Of these the aqueous phase had a high surfactant content, while the organic water-immiscible phase essentially comprised phenyl octyl ether. The organic phase was separated off and replaced by the same weight of octyl bromide. The new mixture resulting by this replacement was heated to 70° C. In this case, two phases formed again. The phase having a high surfactant content was now the organic water-immiscible phase which contained the phenyl octyl ether. The substantially surfactant-free aqueous NaBr solution was separated off and replaced by the same weight of 1 N sodium phenolate solution in water. The reaction mixture formed in this second replacement was again fed to the reaction for the formation of the phenyl octyl ether. The loss of surfactant was approximately 5% of that originally used.

What is claimed is:

1. A method for the work-up of a reaction mixture, present as a microemulsion at a temperature of 0–100° C. and formed in the O-alkylation of phenols by an alkyl halide in the presence of sodium hydroxide, said phenols being present during said O-alkylation as an aqueous solution and said alkyl halide being present during said O-alkylation as a water-immiscible solution in an organic solvent, said O-alkylation taking place in the presence of a nonionic surfactant and said reaction mixture containing, in addition to said surfactant, a first reaction product which is soluble in water and a second reaction product which is insoluble in water and soluble in said organic solvent, said microemulsion being able to be present in coexistence with said aqueous and said organic solutions, wherein the reaction mixture a) is subjected to a temperature change whereby the temperature of the reaction mixture is decreased by 20 to 50K, and by this means an aqueous phase having a high surfactant content and a substantially surfactant-free organic phase are obtained, b) the organic phase, which is substantially surfactant free and contains said second reaction product, is separated off and is replaced by additional organic solution of said alkyl halide, c) the reaction mixture resulting from step b) is subjected to a temperature change whereby the temperature of the reaction mixture is increased by 10 to 80K whereupon a substantially surfactant free aqueous phase and an organic phase having a high surfactant content are obtained, d) the substantially surfactant free aqueous phase, which contains said first reaction product, is separated off and replaced by additional aqueous solution of said phenols, thereby reforming the original reaction mixture of phenols and alkyl halide, the O-alkylation of said phenols by said alkyl halides is repeated and the foregoing work-up process is repeated.

2. The method of claim 1, wherein the microemulsion is present at a temperature of from 30 to 80° C.

3. The method of claim 1, wherein the second temperature change in step c) is by 20 to 60K.

4. The method of claim 1, wherein said nonionic surfactant is selected from the group consisting of alkoxylated phenols and alkoxylated $C_4$–$C_{16}$-alkylphenols.

5. The method of claim 1, wherein the reaction mixture contains 2 to 50% by weight of surfactant, based on the total weight of the reaction mixture.

6. The method of claim 5, wherein the reaction mixture contains 5 to 30% by weight of surfactant, based on the total weight of the reaction mixture.

7. The method of claim 6, wherein the reaction mixture contains 7 to 20% by weight of surfactant, based on the total weight of the reaction mixture.

8. The method of claim 1, wherein the organic phase to be separated off is free of additional solvents.

9. The method of claim 1, wherein in the event of the coexistence of microemulsion and aqueous and organic phase, the amount of the microemulsion represents 50 to 100% by weight of the total reaction mixture, the coexisting aqueous phase represents 35 to 0% by weight of the total reaction mixture and the coexisting organic phase represents 35 to 0% by weight of the total reaction mixture.

10. The method of claim 9, wherein the microemulsion represents 70 to 100% by weight, the coexisting aqueous phase represents 25 to 0% by weight and the coexisting organic phase represents 25 to 0% by weight, all referred to the weight of the total reaction mixture.

* * * * *